United States Patent [19]

Oda et al.

[11] Patent Number: 5,527,897
[45] Date of Patent: Jun. 18, 1996

[54] HUMAN ID GENES

[75] Inventors: Kinichiro Oda; Susumu Nakada; Eiji Hara; Tomoko Yamaguchi, all of Chiba; Takeshi Nakamura, Osaka; Yumiko Oka, Osaka; Toshihiko Kishimoto, Osaka, all of Japan

[73] Assignee: Sumitomo Electric Industries, Ltd., Osaka, Japan

[21] Appl. No.: 151,391

[22] Filed: Nov. 12, 1993

[30] Foreign Application Priority Data

Nov. 13, 1992 [JP] Japan .................................. 4-328391

[51] Int. Cl.$^6$ ........................... C12N 15/00; C12N 15/12
[52] U.S. Cl. .................... 536/23.5; 536/23.1; 435/252.3; 435/320.1
[58] Field of Search ............................. 435/172.3, 69.1, 435/320.1, 252.3–252.35, 240.1, 6; 530/350; 536/23.1, 23.5

[56] References Cited

PUBLICATIONS

Suggs et al, Proc. Natl. Acad. Sci. USA 78: 6613 (1981).
Marcus–Sekura, Anal. Biochem. 172: 289 (1988).
The Protein ID: A Negative Regulator of Helix–Loop–Helix DNA Binding Proteins, Robert Benezra et al., Cell, vol. 61, pp. 49–59, Apr. 1990.
An ID–Related Helix–Loop–Helix Protein Encoded by a Growth Factor–Inducible Gene, Barbara Christy et al., Proc. Natl. Acad. Sci., vol. 88, pp. 1815–1819, Mar. 1991.
A Human ID–Like Helix–Loop–Helix Protein Expressed During Early Development, Joseph Biggs et al., Proc. Natl. Acad. Sci, vol. 89. pp. 1512–1516, Feb. 1992.
B. Kreider et al., "Inhibition of myeloid differentiation by the helix–loop–helix protein Id", Science, vol. 255, 1992, pp. 1700–1702.
J. P. Springhorn et al., "Transcriptional regulation in cardiac muscle", Journal of Biological Chemistry, vol. 267, 1992, pp. 14360–14365.
W. Ellmeier et al., "Mutually exclusive expression of a helix–loop–helix gene and N–myc in human neuroblastomas and in normal development", The EMBO Journal, vol. 11, 1992, pp. 2563–2571.

*Primary Examiner*—James Martinell
*Attorney, Agent, or Firm*—Lowe, Price, LeBlanc & Becker

[57] ABSTRACT

Disclosed herein are Human Id genes (Id-1H and Id-1H') and variants thereof. Origin, preparation process, biochemical functions and the like: two synthetic oligonucleotides separately having base sequences corresponding to regions of amino acid sequence, which are almost completely conserved by three mouse Id genes (Id-1, Id-2 and HLH462) are used as probes to screen clones having respective cDNAs complementary to the probes from a cDNA library of human TIG-1 fibroblasts in accordance with the hybridization method, thereby isolating human Id genes. The expression of the human Id genes specifically varies according to the state of cell proliferation, in particular, the acquisition of cell aging and permanently proliferating ability.

Expression vectors with the human Id gene or variant thereof integrated therein, transformed cell strains with the expression vector introduced therein, diagnostic probes obtained by chemically synthesizing a partial sequence of the base sequence of the human Id gene, or a variation sequence thereof, and antisense oligonucleotides composed of a base sequences complementary to the partial sequence of the base sequence of the human Id gene, or the variation sequence thereof are also disclosed.

10 Claims, 3 Drawing Sheets

5'GATGTAGTC$^G_T$AT$^G_T$ACA$^T_C$GCTGCAGGAT$^T_C$TCCACCT$^T_G$GC3'  (SEQ ID NO:5 [TOP] / SEQ ID NO:6 [BOTTOM])

5'CAG$^C_T$TCC$^{TT}_{CG}$$^G_C$AGGCG$^C_T$GAGTAGCAG$^{TC}_{CG}$GTTCATGT$^C_T$GT3'  (SEQ ID NO:7 [TOP] / SEQ ID NO:8 [BOTTOM])

Time after induction of proliferation (hr)

HUMAN ID GENES

FIELD OF THE INVENTION

The present invention relates to human Id genes, and more particularly to two genes, Id-1H and Id-1H' (both genes will hereinafter be called "human Id genes"), which code for human Id proteins, respectively, expression vectors with the human Id genes separately integrated therein, transformed cell strains with the expression vectors separately introduced therein, recombinant Id proteins obtained by cultivating the respective transformed cells, diagnostic probes composed of respective partial sequences of the base sequences of the human Id genes, or variation sequences thereof, and antisense oligonucleotides composed of respective base sequences complementary to the partial sequences of the base sequences of the human Id genes, or the variation sequences thereof. The antisense oligonucleotides can be used in antisense therapy.

BACKGROUND OF THE INVENTION

An Id protein was found as a myogenic regulatory factor suppressing the activity of a muscle-specific gene in mouse C3H10T1/2 fibroblasts [Cell, Vol. 61, 49–59 (1991)]. A subsequent research revealed that Id proteins are recognized in many kinds of cells during proliferation and decrease upon removal of sera and growth factors, and differentiation of cells [Proc. Natl. Acad. Sci. USA. Vol. 88, 1815–1819 (1991)].

From the above-described facts, the presence of an Id protein in cells and the expression of an Id gene that codes for the Id protein can be positioned as an index for determining the state of cell proliferation, and the state of cell differentiation and aging.

Three kinds of genes, Id-1, Id-2 and HLH462 have presently been known as mouse Id genes. However, only a human Id-2 gene corresponding to the mouse Id-2 gene has heretofore been known as an Id gene present in human cells [Proc. Natl. Acad. Sci. USA, Vol. 89, 1512–1516 (1992)]. Therefore, several unknown human Id genes have been considered to exist. In view of further applications of Id genes and knowledge about the Id genes to fundamental experiments on the human and human cells, diagnoses and therapies, a problem to be early overcome has been to acquire unknown human Id genes.

OBJECTS AND SUMMARY OF THE INVENTION

It is an object of the present invention to provide a novel human Id gene.

Another object of the present invention is to provide an expression vector with the human Id gene integrated therein, a transformed cell strain with the expression vector introduced therein, a recombinant Id protein obtained by cultivating the transformed cells, a diagnostic probe composed of a partial sequence of the base sequence of the human Id gene, or a variation sequence thereof, and an antisense oligonucleotide composed of a base sequence complementary to the partial sequence of the base sequence of the human Id gene, or the variation thereof.

The present inventors have carried out an extensive investigation with a view toward solving the above-described problem. As a result, Id-1H and Id-1H' have been successfully isolated as novel human Id genes corresponding to the mouse Id-1 gene. These two human Id genes are derived from the same genetic locus on a genome by alternate splicing. The isolated human Id gene has been integrated in an expression vector which has then been introduced into *Escherichia coli* cells, thereby successfully producing a recombinant Id protein in a great amount. The present inventors have further found that the expression of the Id-1H and Id-1H' genes specifically varies according to the state of cell proliferation, in particular, the acquisition of cell aging and permanently proliferating ability, and revealed that these Id genes can be used in diagnostic probes and the like, thus leading to completion of the present invention.

According to the present invention, there are thus provided a human Id gene (Id-1H) represented by a base sequence of SEQ ID NO:1 in Sequence Table which will be described subsequently, and a human Id gene (Id-1H') represented by a base sequence of SEQ ID NO:3. These human Id genes include respective variants.

According to the present invention, there are also provided novel expression vectors with the human Id genes, or the variants thereof separately integrated therein, and novel transformed cell strains with the expression vectors separately introduced therein.

According to the present invention, there are further provided recombinant Id proteins obtained by separately cultivating the transformed cell strains.

Diagnostic probes can be obtained by chemically synthesizing a partial sequence of the base sequence of each of the human Id genes, or a variation sequence thereof. When an antisense oligonucleotide composed of a base sequence complementary to the partial sequence of the base sequence of the human Id gene, or the variation sequence thereof is synthesized, it can be used in antisense therapy and the like.

DETAILED DESCRIPTION OF THE INVENTION

The present invention will hereinafter be described in detail.

(1) Isolation of Human Id Gene

The human Id genes (Id-1H and Id-1H') according to the present invention are cDNAs derived from human TIG-1 fibroblasts. Each of these cDNAs can be prepared in the following manner.

An oligonucleotide having a base sequence complementary to a base sequence which is considered to be well-conserved among DNA sequences of three kinds of the known mouse Id genes (Id-1, Id-2 and HLH462) and be indispensable to proteins from the viewpoint of the corelation between their structures and functions is first synthesized. The thus-synthesized oligonucleotide is then used as a probe to screen a clone containing a cDNA complementary to the probe from a cDNA library of the human TIG-1 fibroblasts by the hybridization method, thereby isolating a human Id gene.

Figures 1, 2, 3:
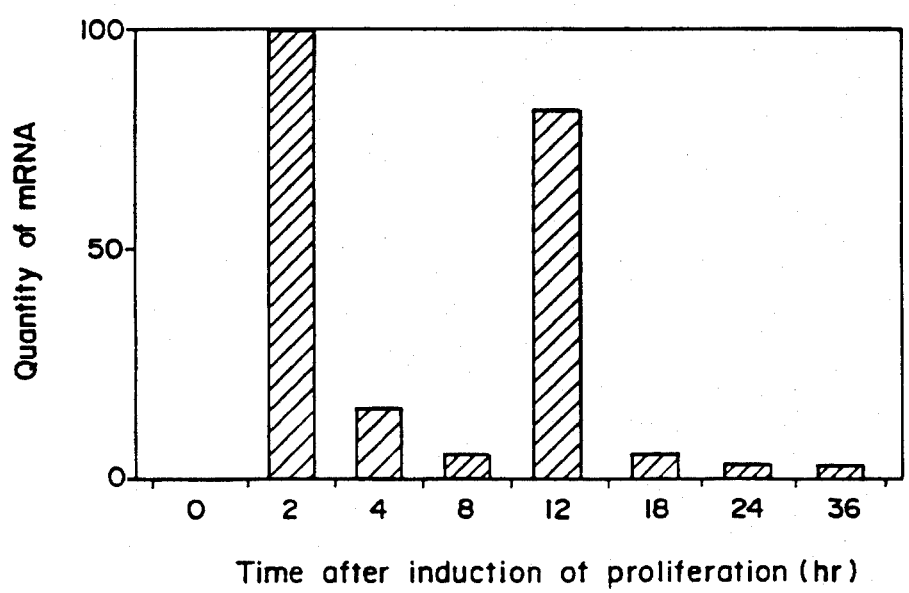
FIG. 1 illustrates a base sequence of an oligonucleotide used as a probe upon screening two human Id genes (Id-1H and Id-1H') from a human cDNA library by the hybridization method.
FIG. 2 illustrates a base sequence of another oligonucleotide used as a probe upon screening two human Id genes (Id-1H and Id-1H') from the human cDNA library by the hybridization method.
FIG. 3 is a graph illustrating variations in quantity of the transcription product by the Id-1H gene in juvenile cells according to the state of proliferation.

Base sequences of two synthetic oligonucleotides (HLH-1 and HLH-2) used as the probes are illustrated in FIGS. 1 and 2, respectively. These two base sequences are base sequences (each 38-mer) corresponding to two regions of amino acid sequence (corresponding to two α-helix portions), which are almost completely conserbed by the three mouse Id genes. Since the synthetic oligonucleotides are synthesized by means of an oligonucleotide synthesizer on the basis of the amino acid sequences, they are obtained as mixtures of those containing different base sequences due to degeneracy, as shown in FIGS. 1 and 2.

With respect to two kinds of the human Id genes thus obtained, all base sequences are determined by the dideoxynucleotide chain-termination method or Maxam-Gilbert method, and their portions required for the expression of the human Id genes are then determined. The base sequence thus determined are shown as Sequence No. 1 (Id-1H) and Sequence No. 2 (Id-1H') in Sequence Table which will be described below. The human Id genes according to the present invention include these two genes, Id-1H and Id-1H' and variants thereof (2) Production of Human Id Gene-integrated Expression Vector, Transformed Cell with the Expression Vector Introduced Therein, and Human Id Protein Each of the human Id genes (cDNAs) isolated in the above-described manner is integrated in a vector by a method known per se in the art. Vectors used may be those lacking for a DNA portion other than a portion required for proliferation in addition to extracts from naturally occurred products. For example, a pET3 vector may preferably be used for mass production of human Id proteins. As a method for integrating the cDNA in the vector DNA, there may be used any known method, for example, treatment of the DNA with an restriction enzyme and reconstitution with a ligase.

The human Id gene-integrated plasmid vector thus obtained is introduced into host microorganisms by a method known per se in the art to obtain a transformed cell strain (transformant). As the host microorganisms to be introduced, it is preferable to use microorganisms (*Escherichia coli*) belonging to *Escherichia* and typified by an *Escherichia coli* K12 strain. If the pET3 vector is used as an expression vector for producing a human Id protein, it is particularly preferable to use BL21(DE3)Lys S as microorganisms to be introduced because impurities derived from *Escherichia coli* remain little in the course of purification, and time and labor can hence be saved.

These transformed cell strains are novel microorganisms obtained by transformation in which a plasmid vector obtained by integrating the human Id gene (cDNA, Id-1H or Id-1H') in a pUC118 plasmid is introduced into the *Escherichia coli* K12 strain and include two strains called "E. coli pId-1H" (NIBHT Deposition FERM BP-4460 deposited in National Institute of Bioscience and Human-Technology, Agency of Industrial Science and Technology, 1–3, Higashi 1 chome Tsukuba-shi Ibaraki-ken 305, Japan: *Escherichia coli* K12 strain) obtained by using Id-1H as cDNA and "E. coli pId-1H'" (NIBHT Deposition FERM BP-4461: *Escherichia coli* K12 strain) obtained by using Id-1H' as cDNA.

Similarly, a transformed cell strain can be obtained by introducing an expression vector, which has been obtained by integrating the human Id gene (cDNA, Id-1H or Id-1H') in an expression vector, for example, a pET3 vector or the like, into *Escherichia coli*, for example, BL21(DE3)Lys S. This strain can be cultivated, thereby obtaining a recombinant Id protein from the resultant culture.

(3) Diagnostic Probe and Antisense Oligonucleotide

The Id proteins are recognized to not only have properties as myogenic regulatory factors which serve to suppress the activity of muscle-specific genes, but also exist widely in actively proliferating cells. The quantity of the Id proteins decreases when proliferation is terminated by removing sera and growth factors or inducing cell differentiation.

Further, the present inventors have newly found that the human Id proteins specifically varies according to the acquisition of cell aging and permanently proliferating ability. Therefore, it is thought that information for determining the state of proliferation, and the state of differentiation and aging in tissues and cells can be obtained by knowing the quantity of Id genes expressed in cells and the presence of mutation of Id loci in genomes, and that a partial sequence of a human Id gene sequence, or a variation sequence thereof can be used as a diagnostic probe.

The Id proteins are also transcriptional regulatory factors existing in nuclei, and there is hence a possibility that they may regulate the expression of a great number of genes participating in cell proliferation in view of their mechanism. In that case, it is thought that the expression of a wide range of genes participating in cell proliferation can be affected by controlling the expression of the Id genes. If a means for effectively inhibiting the synthesis of Id proteins can be found by an antisense technique or the like, a therapeutic means can be provided for diseases, in which proliferation aberration acquires an important significance, such as cancer and progeria. For example, in an experiment making use of cultured cells, cell proliferation can be controlled negatively by inhibiting the expression of an Id gene with an antisense oligonucleotide.

ADVANTAGES OF THE INVENTION

According to the present invention, there are provided novel human Id genes, expression vectors with the human Id genes separately integrated therein, transformed cell strains with the expression vectors separately introduced therein, and the like. The human Id genes according to the present invention are useful in a field of genetic engineering, fundamental experiments on human cells, diagnoses, therapies and the like. For example, they can be expected to apply to diagnostic probes composed of respective partial sequences of the base sequences of the human Id genes, or variation sequences thereof, and antisense therapy using antisense oligonucleotides composed of respective base sequences complementary to the partial sequences of the base sequences of the human Id genes, or the variation sequences thereof.

EMBODIMENTS OF THE INVENTION

The present invention will hereinafter be described more specifically by the following examples.

EXAMPLE 1

(1) Selection and Chemical Synthesis of Base Sequence Used as Probe

In order to isolate human Id genes existing in human cells, amino acid sequences coded by three mouse Id genes (Id-1, Id-2 and HLH462) were investigated to find two regions of amino acid sequence (corresponding to two α-helix portions) which were almost completely conserved by the three mouse Id genes. Two base sequences (each 38-mer) corresponding to the amino acid sequence regions were determined (see FIGS. 1 and 2). Two oligonucleotides (HLH-1 and HLH-2) respectively having the base sequences determined in the above-described manner were synthesized by means of an oligonucleotide synthesizer (380B) manufactured by Applied Biosystems Company.

(2) Construction of Human cDNA Library

A cDNA library was constructed using normal human TIG-1 fibroblasts. The Okayama-Berg method was used in the construction of the cDNA library to obtain a cDNA library composed of 1×10$^6$ colonies.

(3) Cloning of Human Id Gene cDNA

The human cDNA library constructed by the above-described process was screened using, as a probe, a mixture of two kinds of the 38-mer oligonucleotides synthesized in the step (1). The 5' terminal of each of the oligonucleotides was labeled with [γ-$^{32}$P]ATP to hybridize it to a human cDNA fixed to a nylon filter for 16 hours at 65° C. As a reaction solution, was used a mixed solution composed of 5×Denhardt's solution, 5×SSC and 0.5% SDS.

After the hybridization, the filter was washed each twice with (1) a wash of 2×SSC for 10 minutes at room temperature, (2) a wash composed of 2×SSC and 0.1% SDS for 10 minutes at 65° C. and then (3) a wash composed of 0.1×SSC and 0.1% SDS for 5 minutes at room temperature. After drying, exposure was conducted with an X-ray film (Kodak XAR-5) for 7 days at −80° C. Assay was conducted on 10$^6$ colonies, and found to obtain ten positive clones.

(4) Determination of Human Id Gene Base Sequence

Three clones (Clone Nos. 1–3) among the ten clones obtained in the step (3), which did not overlap with each other, were recloned in a pUC118 plasmid. Thereafter, the base sequences of these three clones were determined by means of a Sequenare Version 2 (manufactured by USB Co.) in accordance with the dideoxynucleotide chain-termination method. As a result, it was found that the base sequence of Clone No. 3 is the same as that of the human Id-2 gene already known, but Clone No. 1 and Clone No. 2 are new genes. The base sequence of Clone No. 1 had a homology of 85% to that of the mouse Id gene (Id-1). Therefore, Clone No. 1 was designated as "Id-1H" (H means human). Since Clone No. 2 is considered to be a product created from the same genetic locus as Clone No. 1 by alternate splicing, it was designated as "Id-1H'". The determined base sequences of the Id-1H and Id-1H' genes are shown in Sequence Table which will be described subsequently.

EXAMPLE 2

Preparation of New Microorganisms

With respect to Id-1H, a pCD2 plasmid containing the Id-1H gene derived from the cDNA library constructed in Example 1 was cleaved by an restriction enzyme BamH I to take out an Id-1H cDNA, which was then integrated into a BamH I site of a pCU118 plasmid.

With respect to Id-1H', a pCD2 plasmid containing the Id-1H' gene derived from the cDNA library constructed in Example 1 was cleaved by restriction enzymes BamH I and Kpn I to take out Id-1H' cDNAs, which were then integrated into BamH I and Kpn I sites of a pCU118 plasmid. Thus, two kinds of new microorganisms were obtained. One is E. coli pId-1H (NIBHT Deposition FERM BP-4460) obtained by using Id-1H and the other is E. coli pId-1H' (NIBHT Deposition FERM BP-4461) obtained by using Id-1H'. Similarly, expression vectors obtained by separately integrating the two human Id genes into an expression vector pET3 were introduced into BL21(DE3)Lys S to obtain respective transformed cell strains.

EXAMPLE 3

Figure 4:
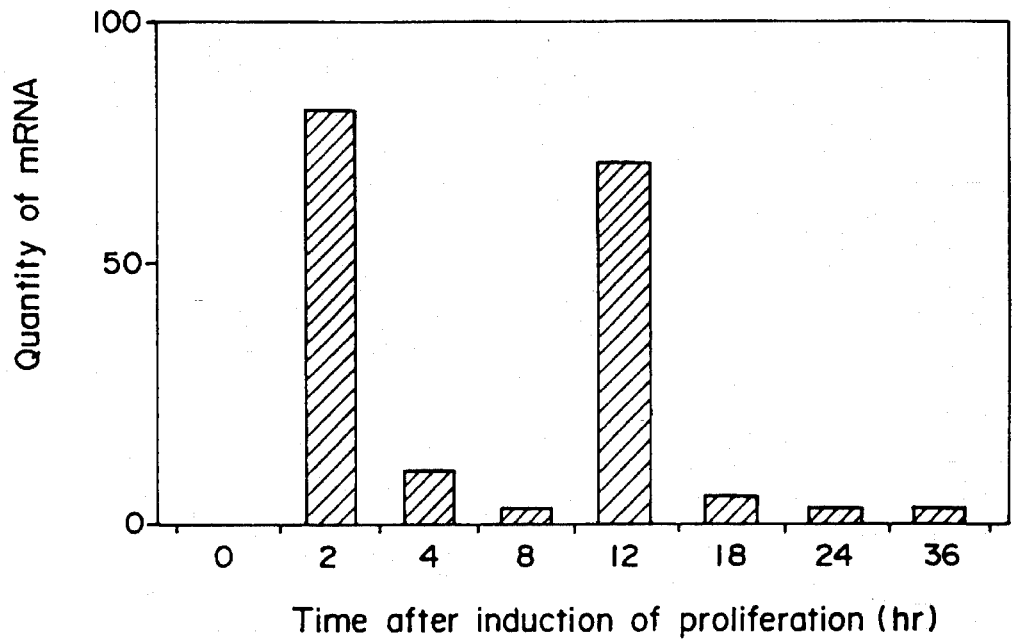
FIG. 4 is a graph illustrating variations in quantity of the transcription product by the Id-1H gene in senile cells according to the state of proliferation.
Figure 5:
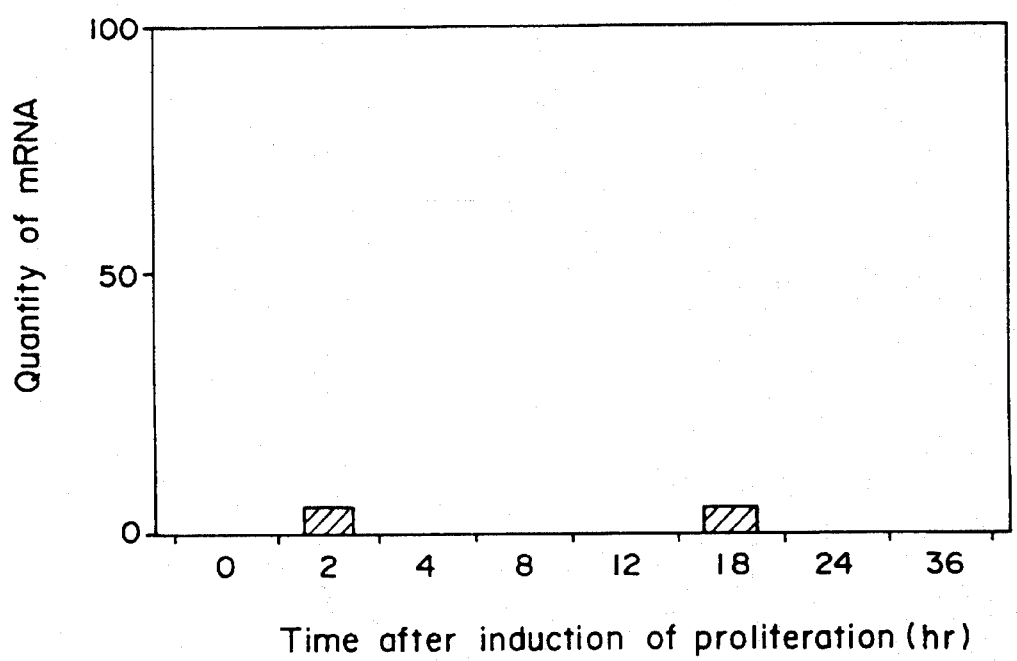
FIG. 5 is a graph illustrating variations in quantity of the transcription product by the Id-1H' gene in juvenile cells according to the state of proliferation.
Figure 6:
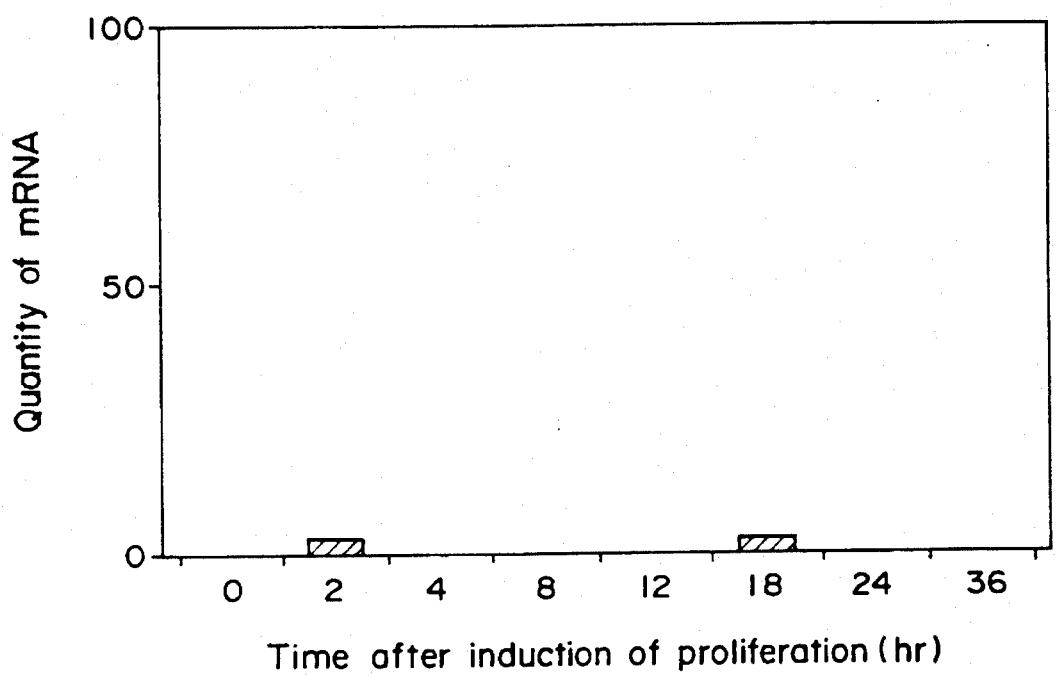
FIG. 6 is a graph illustrating variations in quantity of the transcription product by the Id-1H' gene in senile cells according to the state of proliferation.

Variations in Quantity of the Transcription Product by Id Gene in Cells According to the State of Proliferation Variation in quantity of the transcription products (mRNA) by the Id-1H and Id-1H' genes according to the state of proliferation were determined in accordance with the Northern blot hybridization method (see FIGS. 3 through 6). As illustrated in FIGS. 3 and 4, the quantities of mRNA produced by Id-1H (FIG. 3) and Id-1H' (FIG. 4) as to juvenile cells show specific variation patterns according to the lapse of time. On the contrary, as illustrated in FIGS. 5 and 6, the quantities of mRNA produced by Id-1H (FIG. 5) and Id-1H' (FIG. 6) as to senile cells remain substantially zero corresponding to the fact that the cells come not to respond to proliferative stimulation. These experimental results suggest that the Id-1H and Id-1H' genes bear a certain action in the course of proliferation control and aging.

Therefore, partial sequences of the base sequences of the human Id genes (Id-1H and Id-1H'), or variation sequences thereof are useful as diagnostic probes. If antisense oligonucleotides composed separately of base sequences complementary to the partial sequences of the base sequences of the human Id genes, or the variation sequences thereof are synthesized, they are useful in antisense therapy.

SEQUENCE TABLE

SEQ ID NO: 1
Length of sequence: 509
Type of sequence: nucleic acid
Number of chains: double strand
Topology: linear
Kind of sequence: cDNA to mRNA
Origin:
    Name of organism: Home sapiens
    Kind of cell: TIG-1
Feature of sequence:
    Symbol indicating feature: CDS
    Existing position: 22..486
    Characterizing method: P
Sequence:

```
TTCAGCCAGT CGCCAAGAAT C ATG AAA GTC GCC AGT GGC AGC ACC GCC      48
                         Met Lys Val Ala Ser Gly Ser Thr Ala
```

SEQUENCE TABLE-continued

| | 1 | | | | 5 | | | | | | | | | | | |
|---|---|---|---|---|---|---|---|---|---|---|---|---|---|---|---|---|
| ACC | GCC | GCC | GCG | GGC | CCC | ACG | TGC | GCG | CTG | AAG | GCC | GGC | AAG | ACA | GCG | 96 |
| Thr | Ala | Ala | Ala | Gly | Pro | Thr | Cys | Ala | Leu | Lys | Ala | Gly | Lys | Thr | Ala | |
| 10 | | | | | 15 | | | | | 20 | | | | | 25 | |
| AGC | GGT | GCG | GGC | GAG | GTG | GTG | CGC | TGT | CTG | TCT | GAG | CAG | AGC | GTG | GCC | 144 |
| Ser | Gly | Ala | Gly | Glu | Val | Val | Arg | Cys | Leu | Ser | Glu | Gln | Ser | Val | Ala | |
| | | | | 30 | | | | 35 | | | | | | 40 | | |
| ATC | TCG | CGC | TGC | CGG | GGC | GCC | GGG | GCG | CGC | CTG | CCT | GCC | CTG | CTG | GAC | 192 |
| Ile | Ser | Arg | Cys | Arg | Gly | Ala | Gly | Ala | Arg | Leu | Pro | Ala | Leu | Leu | Asp | |
| | | | 45 | | | | | 50 | | | | | | 55 | | |
| GAG | CAG | CAG | GTA | AAC | GTG | CTG | CTC | TAC | GAC | ATG | AAC | GGC | TGT | TAC | TCA | 240 |
| Glu | Gln | Gln | Val | Asn | Val | Leu | Leu | Tyr | Asp | Met | Asn | Gly | Cys | Tyr | Ser | |
| | | 60 | | | | | 65 | | | | | 70 | | | | |
| CGC | CTC | AAG | GAG | CTG | GTG | CCC | ACC | CTG | CCC | CAG | AAC | CGC | AAG | GTG | AGC | 288 |
| Arg | Leu | Lys | Glu | Leu | Val | Pro | Thr | Leu | Pro | Gln | Asn | Arg | Lys | Val | Ser | |
| | 75 | | | | | 80 | | | | | 85 | | | | | |
| AAG | GTG | GAG | ATT | CTC | CAG | CAC | GTC | ATC | GAC | TAC | ATC | AGG | GAC | CTT | CAG | 336 |
| Lys | Val | Glu | Ile | Leu | Gln | His | Val | Ile | Asp | Tyr | Ile | Arg | Asp | Leu | Gln | |
| 90 | | | | | 95 | | | | | 100 | | | | | 105 | |
| TTG | GAG | CTG | AAC | TCG | GAA | TCC | GAA | GTT | GGA | ACC | CCC | GGG | GGC | CGA | GGG | 384 |
| Leu | Glu | Leu | Asn | Ser | Glu | Ser | Glu | Val | Gly | Thr | Pro | Gly | Gly | Arg | Gly | |
| | | | | 110 | | | | | 115 | | | | | 120 | | |
| CTG | CCG | GTC | CGG | GCT | CCG | CTC | AGC | ACC | CTC | AAC | GGC | GAG | ATC | AGC | GCC | 432 |
| Leu | Pro | Val | Arg | Ala | Pro | Leu | Ser | Thr | Leu | Asn | Gly | Glu | Ile | Ser | Ala | |
| | | | 125 | | | | | 130 | | | | | 135 | | | |
| CTG | ACG | GCC | GAG | GCG | GCA | TGC | GTC | CCT | GCG | GAC | GAT | CGC | ATC | TTG | TGT | 480 |
| Leu | Thr | Ala | Glu | Ala | Ala | Cys | Val | Pro | Ala | Asp | Asp | Arg | Ile | Leu | Cys | |
| | | | 140 | | | | 145 | | | | | 150 | | | | |
| CGC | TGAAGGCCTT | | CCCCAGGGAC | | | CGGCGG | | | | | | | | | | 509 |
| Arg | | | | | | | | | | | | | | | | |

SEQ ID NO: 3
Length of sequence: 502
Type of sequence: nucleic acid
Number of chains: double strand
Topology: linear
Kind of sequence: cDNA to mRNA
Origin:
    Name of organism: Home sapiens
    Kind of cell: TIG-1
Feature of sequence:
    Symbol indicating feature: CDS
    Existing position: 22..486
    Characterizing method: P
Sequence:

| TTCAGCCAGT | CGCCAAGAAT | C | ATG | AAA | GTC | GCC | AGT | GGC | AGC | ACC | GCC | | 48 |
|---|---|---|---|---|---|---|---|---|---|---|---|---|---|
| | | | Met | Lys | Val | Ala | Ser | Gly | Ser | Thr | Ala | | |
| | | | 1 | | | | 5 | | | | | | |
| ACC | GCC | GCC | GCG | GGC | CCC | ACG | TGC | GCG | CTG | AAG | GCC | GGC | AAG | ACA | GCG | 96 |
| Thr | Ala | Ala | Ala | Gly | Pro | Thr | Cys | Ala | Leu | Lys | Ala | Gly | Lys | Thr | Ala | |
| 10 | | | | | 15 | | | | | 20 | | | | | 25 | |
| AGC | GGT | GCG | GGC | GAG | GTG | GTG | CGC | TGT | CTG | TCT | GAG | CAG | AGC | GTG | GCC | 144 |
| Ser | Gly | Ala | Gly | Glu | Val | Val | Arg | Cys | Leu | Ser | Glu | Gln | Ser | Val | Ala | |
| | | | | 30 | | | | 35 | | | | | | 40 | | |
| ATC | TCG | CGC | TGC | CGG | GGC | GCC | GGG | GCG | CGC | CTG | CCT | GCC | CTG | CTG | GAC | 192 |
| Ile | Ser | Arg | Cys | Arg | Gly | Ala | Gly | Ala | Arg | Leu | Pro | Ala | Leu | Leu | Asp | |
| | | | 45 | | | | | 50 | | | | | | 55 | | |
| GAG | CAG | CAG | GTA | AAC | GTG | CTG | CTC | TAC | GAC | ATG | AAC | GGC | TGT | TAC | TCA | 240 |
| Glu | Gln | Gln | Val | Asn | Val | Leu | Leu | Tyr | Asp | Met | Asn | Gly | Cys | Tyr | Ser | |
| | | 60 | | | | | 65 | | | | | 70 | | | | |
| CGC | CTC | AAG | GAG | CTG | GTG | CCC | ACC | CTG | CCC | CAG | AAC | CGC | AAG | GTG | AGC | 288 |
| Arg | Leu | Lys | Glu | Leu | Val | Pro | Thr | Leu | Pro | Gln | Asn | Arg | Lys | Val | Ser | |
| | 75 | | | | | 80 | | | | | 85 | | | | | |
| AAG | GTG | GAG | ATT | CTC | CAG | CAC | GTC | ATC | GAC | TAC | ATC | AGG | GAC | CTT | CAG | 336 |
| Lys | Val | Glu | Ile | Leu | Gln | His | Val | Ile | Asp | Tyr | Ile | Arg | Asp | Leu | Gln | |
| 90 | | | | | 95 | | | | | 100 | | | | | 105 | |

| | | | | | | | | | | | | | | | | |
|---|---|---|---|---|---|---|---|---|---|---|---|---|---|---|---|---|
| TTG | GAG | CTG | AAC | TCG | GAA | TCC | GAA | GTT | GGA | ACC | CCC | GGG | GGC | CGA | GGG | 384 |
| Leu | Glu | Leu | Asn | Ser 110 | Glu | Ser | Glu | Val | Gly 115 | Thr | Pro | Gly | Gly | Arg 120 | Gly | |
| CTG | CCG | GTC | CGC | GCT | CCG | CTC | AGC | ACC | CTC | AAC | GGC | GAG | ATC | AGT | GCC | 432 |
| Leu | Pro | Val | Arg 125 | Ala | Pro | Leu | Ser | Thr 130 | Leu | Asn | Gly | Glu | Ile 135 | Ser | Ala | |
| CTG | ACG | GCC | GAG | GTG | AGA | TCC | AGA | TCC | GAC | CAC | TAGATCATCC | | | | | 480 |
| Leu | Thr | Ala 140 | Glu | Val | Arg | Ser | Arg 145 | Ser | Asp | His | | | | | | |
| | TTATACCGAC | | | GGGGAAACGG | | | AGGCCAG | | | | | | | | | 502 |

---

We claim:

1. A recombinant DNA comprising a human Id gene (Id-1H) having a sequence as set forth in SEQ ID NO:1.

2. An expression vector with the human Id gene (Id-1H) as claimed in claim 1 integrated therein.

3. A transformed cell strain with the expression vector as claimed in claim 2 introduced therein.

4. A diagnostic probe to determine the state of proliferation, differentiation or aging in tissues or cells obtained by chemically synthesizing a partial sequence of the base sequence of the human Id gene (Id-1H) as claimed in claim 1; wherein said probe has a sequence selected from the group consisting of SEQ ID NO:5 and SEQ ID NO:6.

5. An antisense oligonucleotide composed of a base sequence complementary to a partial sequence of the base sequence of the human Id gene (Id-1H) as claimed in claim 4.

6. A recombinant DNA comprising a human Id gene (Id-1H') having a sequence as set forth in SEQ ID NO:3.

7. An expression vector with the human Id gene (Id-1H') as claimed in claim 6 integrated therein.

8. A transformed cell strain with the expression vector as claimed in claim 7 introduced therein.

9. A diagnostic probe to determine the state of proliferation, differentiation or aging in tissues or cells obtained by chemically synthesizing a partial sequence of the base sequence of the human Id gene (Id-1H') as claimed in claim 1; wherein said probe has a sequence selected from the group consisting of SEQ ID NO:7 and SEQ ID NO:8.

10. An antisense oligonucleotide composed of a base sequence complementary to a partial sequence of the base sequence of the human Id gene (Id-1H') as claimed in claim 9.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 509 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Homo sapiens ( i x ) FEATURE:
        ( A ) NAME/KEY: misc_feature
        ( B ) LOCATION: 22..483
        ( D ) OTHER INFORMATION: /note="CDS"

( x i ) SEQUENCE DESCRIPTION: SEQ ID NO:1:

| | | | | | | |
|---|---|---|---|---|---|---|
| TTCAGCCAGT | CGCCAAGAAT | CATGAAAGTC | GCCAGTGGCA | GCACCGCCAC | CGCCGCCGCG | 60 |
| GGCCCCACGT | GCGCGCTGAA | GGCCGGCAAG | ACAGCGAGCG | GTGCGGGCGA | GGTGGTGCGC | 120 |
| TGTCTGTCTG | AGCAGAGCGT | GGCCATCTCG | CGCTGCCGGG | GCGCCGGGGC | GCGCCTGCCT | 180 |
| GCCCTGCTGG | ACGAGCAGCA | GGTAAACGTG | CTGCTCTACG | ACATGAACGG | CTGTTACTCA | 240 |
| CGCCTCAAGG | AGCTGGTGCC | CACCCTGCCC | CAGAACCGCA | AGGTGAGCAA | GGTGGAGATT | 300 |
| CTCCAGCACG | TCATCGACTA | CATCAGGGAC | CTTCAGTTGC | AGCTGAACTC | GGAATCCGAA | 360 |
| GTTGGAACCC | CCGGGGGCCG | AGGGCTGCCG | GTCCGGGCTC | CGCTCAGCAC | CCTCAACGGC | 420 |
| GAGATCAGCG | CCCTGACGGC | CGAGGCGGCA | TGCGTCCCTG | CGGACGATCG | CATCTTGTGT | 480 |
| CGCTGAAGGC | CTTCCCCAGG | GACCGGCGG | | | | 509 |

( 2 ) INFORMATION FOR SEQ ID NO:2:

( i ) SEQUENCE CHARACTERISTICS:
        ( A ) LENGTH: 154 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:2:

```
Met Lys Val Ala Ser Gly Ser Thr Ala Thr Ala Ala Ala Gly Pro Thr
1               5                   10                  15

Cys Ala Leu Lys Ala Gly Lys Thr Ala Ser Gly Ala Gly Glu Val Val
            20                  25                  30

Arg Cys Leu Ser Glu Gln Ser Val Ala Ile Ser Arg Cys Arg Gly Ala
        35                  40                  45

Gly Ala Arg Leu Pro Ala Leu Leu Asp Glu Gln Gln Val Asn Val Leu
    50                  55                  60

Leu Tyr Asp Met Asn Gly Cys Tyr Ser Arg Leu Lys Glu Leu Val Pro
65                  70                  75                  80

Thr Leu Pro Gln Asn Arg Lys Val Ser Lys Val Glu Ile Leu Gln His
                85                  90                  95

Val Ile Asp Tyr Ile Arg Asp Leu Gln Leu Glu Leu Asn Ser Glu Ser
            100                 105                 110

Glu Val Gly Thr Pro Gly Gly Arg Gly Leu Pro Val Arg Ala Pro Leu
        115                 120                 125

Ser Thr Leu Asn Gly Glu Ile Ser Ala Leu Thr Ala Glu Ala Ala Cys
    130                 135                 140

Val Pro Ala Asp Asp Arg Ile Leu Cys Arg
145                 150
```

( 2 ) INFORMATION FOR SEQ ID NO:3:

( i ) SEQUENCE CHARACTERISTICS:
( A ) LENGTH: 502 base pairs
( B ) TYPE: nucleic acid
( C ) STRANDEDNESS: double
( D ) TOPOLOGY: linear ( i i ) MOLECULE TYPE: cDNA to mRNA ( i i i ) HYPOTHETICAL: NO ( i v ) ANTI-SENSE: NO ( i x ) FEATURE:
( A ) NAME/KEY: misc_feature
( B ) LOCATION: 22..465
( D ) OTHER INFORMATION: /note="CDS"

( x i ) SEQUENCE DESCRIPTION: SEQ ID NO:3:

| | | | | | | |
|---|---|---|---|---|---|---|
| TTCAGCCAGT | CGCCAAGAAT | CATGAAAGTC | GCCAGTGGCA | GCACCGCCAC | CGCCGCCGCG | 60 |
| GGCCCCACGT | GCGCGCTGAA | GGCCGGCAAG | ACAGCGAGCG | GTGCGGGCGA | GGTGGTGCGC | 120 |
| TGTCTGTCTG | AGCAGAGCGT | GGCCATCTCG | CGCTGCCGGG | GCGCCGGGGC | GCGCCTGCCT | 180 |
| GCCCTGCTGG | ACGAGCAGCA | GGTAAACGTG | CTGCTCTACG | ACATGAACGG | CTGTTACTCA | 240 |
| CGCCTCAAGG | AGCTGGTGCC | CACCCTGCCC | CAGAACCGCA | AGGTGAGCAA | GGTGGAGATT | 300 |
| CTCCAGCACG | TCATCGACTA | CATCAGGGAC | CTTCAGTTGG | AGCTGAACTC | GGAATCCGAA | 360 |
| GTTGGAACCC | CCGGGGGCCG | AGGGCTGCCG | GTCCGCGCTC | CGCTCAGCAC | CCTCAACGGC | 420 |
| GAGATCAGTG | CCCTGACGGC | CGAGGTGAGA | TCCAGATCCG | ACCACTAGAT | CATCCTTATA | 480 |
| CCGACGGGGA | AACGGAGGCC | AG | | | | 502 |

( 2 ) INFORMATION FOR SEQ ID NO:4:

( i ) SEQUENCE CHARACTERISTICS:
( A ) LENGTH: 148 amino acids
( B ) TYPE: amino acid
( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:4:

| Met | Lys | Val | Ala | Ser | Gly | Ser | Thr | Ala | Thr | Ala | Ala | Ala | Gly | Pro | Thr |
|---|---|---|---|---|---|---|---|---|---|---|---|---|---|---|---|
| 1 | | | | 5 | | | | | 10 | | | | | 15 | |
| Cys | Ala | Leu | Lys | Ala | Gly | Lys | Thr | Ala | Ser | Gly | Ala | Gly | Glu | Val | Val |
| | | | 20 | | | | | 25 | | | | | 30 | | |
| Arg | Cys | Leu | Ser | Glu | Gln | Ser | Val | Ala | Ile | Ser | Arg | Cys | Arg | Gly | Ala |
| | | | 35 | | | | 40 | | | | | 45 | | | |
| Gly | Ala | Arg | Leu | Pro | Ala | Leu | Leu | Asp | Glu | Gln | Val | Asn | Val | Leu | |
| | 50 | | | | | 55 | | | | | 60 | | | | |
| Leu | Tyr | Asp | Met | Asn | Gly | Cys | Tyr | Ser | Arg | Leu | Lys | Glu | Leu | Val | Pro |
| 65 | | | | | 70 | | | | | 75 | | | | | 80 |
| Thr | Leu | Pro | Gln | Asn | Arg | Lys | Val | Ser | Lys | Val | Glu | Ile | Leu | Gln | His |
| | | | | 85 | | | | | 90 | | | | | 95 | |
| Val | Ile | Asp | Tyr | Ile | Arg | Asp | Leu | Gln | Leu | Glu | Leu | Asn | Ser | Glu | Ser |
| | | | 100 | | | | | 105 | | | | | 110 | | |
| Glu | Val | Gly | Thr | Pro | Gly | Gly | Arg | Gly | Leu | Pro | Val | Arg | Ala | Pro | Leu |
| | | 115 | | | | | 120 | | | | | 125 | | | |
| Ser | Thr | Leu | Asn | Gly | Glu | Ile | Ser | Ala | Leu | Thr | Ala | Glu | Val | Arg | Ser |
| | 130 | | | | | 135 | | | | | 140 | | | | |
| Arg | Ser | Asp | His | | | | | | | | | | | | |
| 145 | | | | | | | | | | | | | | | |

( 2 ) INFORMATION FOR SEQ ID NO:5:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:5:

GATGTAGTCG ATGACATGCT GCAGGATTTC CACCTTGC      38

( 2 ) INFORMATION FOR SEQ ID NO:6:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:6:

GATGTAGTCT ATTACACGCT GCAGGATCTC CACCTGGC      38

( 2 ) INFORMATION FOR SEQ ID NO:7:

(i) SEQUENCE CHARACTERISTICS:
  (A) LENGTH: 38 base pairs
  (B) TYPE: nucleic acid
  (C) STRANDEDNESS: single
  (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:7:

CAGCTCCTTG AGGCGCGAGT AGCAGTCGTT CATGTCGT   38

(2) INFORMATION FOR SEQ ID NO:8:

(i) SEQUENCE CHARACTERISTICS:
  (A) LENGTH: 38 base pairs
  (B) TYPE: nucleic acid
  (C) STRANDEDNESS: single
  (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:8:

CAGTTCCCGC AGGCGTGAGT AGCAGCGGTT CATGTTGT   38